United States Patent
Bard

(10) Patent No.: US 6,828,143 B1
(45) Date of Patent: Dec. 7, 2004

(54) NANOSCALE CHEMICAL SYNTHESIS

(75) Inventor: Allen J. Bard, Austin, TX (US)

(73) Assignee: Integrated Chemical Synthesizers, Inc., Gaithersburg, MD (US)

( * ) Notice: Subject to any disclaimer, the term of this patent is extended or adjusted under 35 U.S.C. 154(b) by 0 days.

(21) Appl. No.: 08/660,955

(22) Filed: Jun. 10, 1996

Related U.S. Application Data

(63) Continuation-in-part of application No. 08/221,931, filed on Apr. 1, 1994, now Pat. No. 5,580,523.

(51) Int. Cl.$^7$ .......................... G01N 33/00; B01J 10/00; F27B 15/00; C12M 1/00
(52) U.S. Cl. ............................... 435/289.1; 435/283.1; 435/292.1; 435/305.1; 435/DIG. 43; 422/50; 422/129; 422/131; 422/134; 422/141; 422/142
(58) Field of Search .......................... 435/289.1, 810, 435/283.1, 292.1, 305.1, DIG. 43; 422/50, 68.1, 129, 131, 134, 141, 142, 70, 81, 82.01, 82.05, 99, 108, 110, 116, 119; 210/198.2; 73/61.16

(56) References Cited

U.S. PATENT DOCUMENTS

| | | | |
|---|---|---|---|
| 4,095,953 A | * | 6/1978 | Gutterman et al. ....... 23/277 R |
| 4,160,803 A | * | 7/1979 | Potts ......................... 422/101 |
| 4,292,409 A | * | 9/1981 | Cremonesi ................ 435/288 |
| 4,476,089 A | * | 10/1984 | Muller-Frank .............. 376/381 |
| 4,638,444 A | * | 1/1987 | Laragione et al. .......... 364/510 |
| 5,132,012 A | * | 7/1992 | Miura et al. ............. 210/198.2 |
| 5,194,133 A | * | 3/1993 | Clark et al. ................. 204/299 |
| 5,246,855 A | * | 9/1993 | Katinger et al. ............ 435/289 |
| 5,296,375 A | * | 3/1994 | Kricka et al. ............... 435/291 |
| 5,304,487 A | * | 4/1994 | Wilding et al. ............. 435/291 |
| 5,385,712 A | * | 1/1995 | Sprunk ....................... 422/190 |
| 5,480,614 A | * | 1/1996 | Kamahori .................... 422/70 |
| 5,580,523 A | * | 12/1996 | Bard ............................ 422/50 |
| 5,603,351 A | * | 2/1997 | Cherukuri et al. .......... 137/597 |

OTHER PUBLICATIONS

Wang et al, Thin Solid Films, 242 (1994), 127–131.*
Harrison et al, Science, vol. 261, (Aug. 13, 1993), pp. 895–897.*

* cited by examiner

*Primary Examiner*—Padmashri Ponnaluri
(74) *Attorney, Agent, or Firm*—Barry Evans, Esq.; Kramer Levin Naftalis & Frankel LLP

(57) ABSTRACT

A modular reactor system and method for synthesizing nanoscale quantities of chemical compounds characterized by a continuous flow reactor under high pressure having uniform temperature throughout the reaction mixture. The apparatus includes a number of generic components such as pumps, flow channels, manifolds, flow restrictors, valves and at least one modular reactor, as small as one nanoliter in volume, where larger quantities can be produced by either using larger nanoscale sized units or adding parallel and serially disposed nanoscale reactor units.

23 Claims, 8 Drawing Sheets

NANOSCALE CHEMICAL SYNTHESIS

CROSS-REFERENCE TO RELATED APPLICATIONS

This application is a continuation-in-part of U.S. patent application Ser. No. 08/221,931, filed Apr. 1, 1994, now U.S. Pat. No. 5,580,523 the entirety of which in incorporated herein by reference.

FIELD OF THE INVENTION

This invention relates to a method and apparatus for nanoscale synthesis of chemical compounds in continuous flow systems with controlled and regulated reaction conditions. More particularly, this invention relates to a modular multi-component nanoscale system with interchangeable nanoreactors, where the nanoreactors are used in tandem, series, or individually for nanoscale synthesis and is adaptable to prepare up to milligram quantities of desired compounds by adding additional reactor units.

BACKGROUND OF THE INVENTION

Organic and inorganic reactions are usually conducted in reaction vessels that typically hold between 0.5 and 1000 mL of reactants in a research laboratory to commercial reactors holding more than 1000 L. Complex inorganic and organic compounds, e.g., drugs, monomers, organometallic compounds, semi-conductors, polymers, peptides, oligonucleotides, polynucleotides, carbohydrates, amino acids, and nucleic acids belong to a class of materials having significant diagnostic, medicinal and commercial importance. However, the systems necessary to carry out and prepare or synthesize these complex materials are inefficient, wasteful and often times require reagent quantities far in excess of what is available. This is especially the case in those instances where milliliter to liter or larger quantities are involved.

The production of these complex materials requires a versatile system that can handle different reaction and separatory schemes. Most synthesizers provide only for a single type of reactor, e.g., electrochemical, catalytic, solid phase support, enzyratic, photochemical, or hollow chamber. These systems are exemplified by the following:

U.S. Pat. No. 4, 517,338 (Urdea) teaches a system for sequencing amino acids with similar reaction zones having an internal diameter (I.D.) of a 0.1 to 1.0 cm;

U.S. Pat. No. 4,960,566 (Mochida) describes an automatic analyzer and process for serial processing of reaction tubes of a common design;

U.S. Pat. No. 4,362,699 (Verlander et al.) teaches high pressure peptide synthesizers and uses a plurality of reservoirs that communicate via a switching valve to a reactor 90;

U.S. Pat. No. 4,458,066 (Caruthers et al.) teaches an amino acid synthesizer with reactor column 10 including a solid silica gel approximately 1 ml. volume in size; and U.S. Pat. No. 4,728,502 (Hamill) relates to a stacked disk amino acid sequencer.

SUMMARY OF THE INVENTION

The present invention provides an Integrated Chemical Synthesis (ICS) system that is modular in design and is capable of nanoliter (nanoscale) size or microscale size processing via continuous flow or batch operation. The modular nature of the system allows for the use of one or more of the same type of reactors, or a variety of different types of reactors, preferably having nanoscale capacity, but capable of using microscale reactors. The nanoscale reactors of the present invention are capable of being used individually, together, and interchangeably with one another and can be of the thermal electrochemical catalytic, enzymatic, photochemical, or hollow chamber type. The modular nature of the system, component parts, e.g., the reactors, flow channels, sensors, detectors, temperature control units, allows easy addition, replacement and/or interchangeability of the component parts.

Other generic components that are included within this invention are flow components (ie., pumps, valves, manifolds, etc.), mixers, separation chambers, heat transfer elements, resistance, ultrasonic or electromagnetic radiation (U.V., I.R., or visible) sources, heaters and/or analyzers. The components are assembled on a support system, e.g., a chip or board, to form a complete nanoscale system and then replicated many times to produce the synthesizer of the desired scale.

The advantage of a nanoscale synthesizer is better yields of products with less waste and disposal problems because of better control of reaction variables. For example, a cylindrical (capillary) reactor with an internal diameter of 100 mm, 1 cm long, with a cell volume of about 0.08 mL. At a linear flow velocity of 0.1 cm/s, the transit time through the cell would be 10 s, and the volume flow would $8 \times 10^{-3}$ mL/s. If conversion of a 1 M solution reactant was complete in this time, then the output of the cell would be 8 nmol product/s. For a product with a molecular weight of 100 g/mol, this would be equivalent to about 3 mg/h or 25 g/year of product. Thus, a bench-sized reactor consisting of 1000 nanoscale synthesis units would produce 69 g/day, while a larger reactor with 176,000 units would be needed to produce 11 kg/year. Considerable yields would require, however, the use of a large number of parallel systems, and to justify their use, the unit cost of each must be very small and their assembly fast and easy.

As a result of the present nanoscale synthesis modular system, the problems of inefficiency, lack of versatility, down-time, reagent/reactant waste and excessive cost have been overcome.

Accordingly, the present invention provides a nanoscale system for synthesizing chemical compounds that is easily upgraded to produce larger quantities of compounds if desired. The system of the present invention can also synthesize compounds under a variety of process conditions, e.g., uniform temperature in a continuous flow reactor under high pressure, non-uniform temperatures and high pressure.

One aspect of the present invention is the use of nanoscale size reactors for combinatorial synthesis, since nanoreactor and nanosystem design allows for the production of small quantities of pure materials for testing.

In accordance with another aspect of the present invention, a modular multicomponent system is provided. The system, e.g. a kit, provides a reaction system capable of handling a variety of reactions by using a reactor unit having a reaction chamber with an I.D. of less than about 0.01 mm up to about 1 mm, and more preferably 0.1 mm–100 mm, most preferably 0.1 mm to 10 mm. Specifically, a modular "chip" type reactor unit is formed by applying a photo-resist layer onto an upper surface of a $SiO_2$ or Si substrate and forming a reactor design thereon. The reactor design is developed and etched with acid to form a reactor chamber having an internal diameter of less than 100 mm. The chamber is covered and the unit mounted on an assembly board containing fluid conveying channels, with fastening means, to provide for flow to and from the reactor chamber.

In accordance with another aspect of the present invention, a modular multicomponent system containing a plurality of interchangeable reaction vessels, alike or different, in parallel or series, and capable of handling reaction volumes of at least 0.1 nL or from about 0.01 nL up to about 10 mL, and more preferably 1 nL–1 mL is provided.

In yet another aspect of the present invention, a system capable of regulating extreme conditions (e.g., supercritical temperatures and pressures) is provided and therefore avoids potential explosions and, provides a reliable method for heat dissipation.

These and other features, aspects and objects will become more apparent in view of the following detailed description, examples and annexed drawings.

DETAILED DESCRIPTION OF THE INVENTION

Figure 1A:
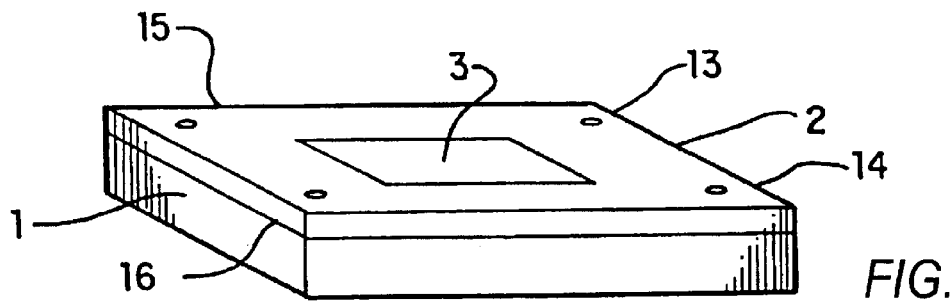
FIG. 1a–1d show a fabricated chip type reactor unit for the ICS modular system.
Figure 1B:
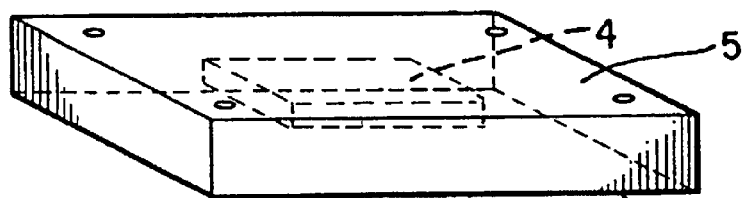
Figure 1C:
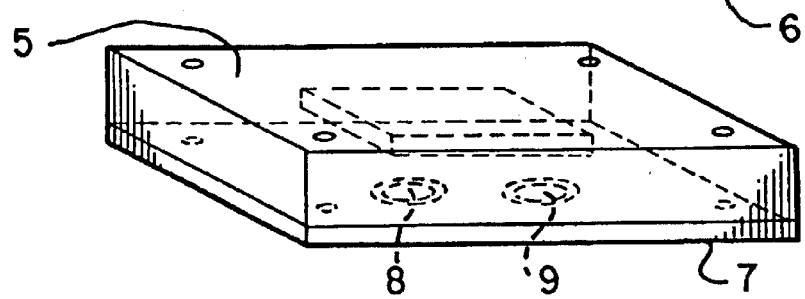
Figure 1D:
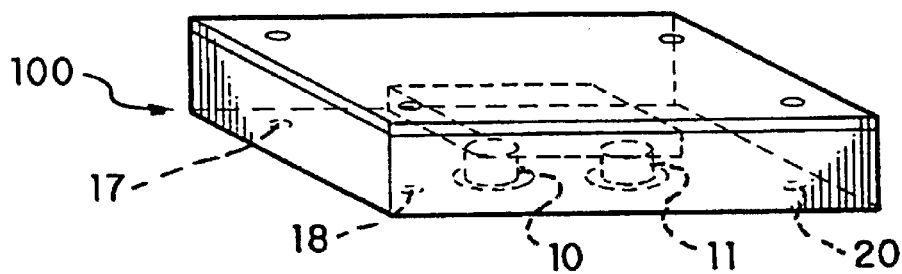

The present invention is broadly directed towards a total modular system that can use a plurality of replaceable and interchangeable nanoscale reactors. Reducing the size of the reactor, i.e., reaction vessel to enable synthesis on a nanoscale has many benefits. Increased surface area to volume, more efficient heat transfer and simplified thermal control of reaction temperature is vastly simplified. Heat transfer depends on the ratio of surface area, A, to volume, V. This is a significant advantage, for example, in comparing small scale capillary-zone electrophoresis (CZE) to large scale gel electrophoresis:

compare (in a 100 $\mu$m cylindrical reactor): $A/V \subseteq 2/r \approx 400$ cm$^{-1}$ with (in a 1-L spherical flask): $A/V \subseteq 3/r \approx 0.5$ cm$^{-1}$ For the same reason, external heating of the nanoreactor and heat dissipation is faster and the maintenance of uniform temperatures throughout the reaction mixture readily accomplished.

It is easier to work at high pressures with small reactors. Super-critical fluids, for example, particularly those involving high temperatures and pressures, are difficult to study in large volumes, often requiring elaborate safety measures and heavy-duty equipment. The smaller scale reactors facilitate the study of near critical and supercritical water solutions at temperatures up to 390° C. and pressures of 240 bar in a 0.238-cm-I.D. (inner diameter) alumina tube. Consequently, reactions may be conducted under conditions of temperature and pressure that are not commercially feasible for large scale synthesis.

The modular nature of the nanoscale synthesizer also imparts to this system certain advantages over more conventional chemical synthetic methods. Easy scale up of reactions based on the nanoscale synthesis approach is attained by simply adding additional modules of exactly the same type to increase output. For industrial synthesis, this would eliminate proceeding from a bench-scale reaction through a very different pilot-plant configuration to a full-size reactor. Inherent redundancy of multiple parallel nanoscale synthesis reactors implies fewer operational problems, since failed reactors can be replaced without shutting down the entire system. This modular system is inherently much safer as well. The rupture of a single nanoscale synthesizer, even at high temperature and pressure, would cause minimal damage, since the total volume and amounts released would be tiny.

The nanoscale synthesis system of the present invention can include a plurality of individual, detachable reactor units. A variety of different reactors are provided to conduct the basic reactions to develop nanoscale synthetic technology. With a plurality of units, one of the reaction units may be structurally different and capable of permitting a different chemical process. Preferably there may be thermal, photochemical, acid/base, redox electrochemical, thermal or pressure units. The thermal and photochemical reactors require that a heat or light source be focused upon the reactor. An acid/base reactor requires introduction of a suitable acid or base catalyst on a polymer support. The catalyst could also be coated on the internal wall surface of the reactor unit. Reagents used in nanoscale HPLC, which is available, can be adapted for the nanoscale reactors of the present invention. The reactors and other nanoscale synthesis components will be fabricated using lithography techniques, e.g., on glass slides or Si substrates, as described below.

Generally, the nanoscale synthesis system includes (1) fluid flow handling and control components; (2) mixers; (3) pumps; (4) reactor "chip type" units; (5) separatory devices; (6) process variable and/or component detectors and controllers; and (7) a computer interface for communicating with a master control center.

Because the flow systems connecting the reactors and other components of the nanoscale manufacturing plant will be fabricated on chips, identification of the products that emerge from specific outlets is straight-forward; the high synthetic and operational overhead associated with "tagging" each compound in a combinatorial library is thus avoided. Combinatorial synthesis involves the development of a synthetic strategy to allow the preparation of a large number of compounds with different structures by assembling several different chemical building blocks into many combinations. The collection of compounds so generated is called a combinatorial library. Such libraries have been of interest in the development of new drugs, catalytic antibodies, and materials. Combinatorial chemistry has been broadly defined as the generation of numerous organic compounds through rapid simultaneous, parallel, or automated synthesis. Analytical control over the chemistry is a significant advantage in developing smaller, more focused libraries. Ultimately, the control over the chemistry will result in the more rapid discovery and development of drugs by researchers in academia and/or in business settings. And finally, since the reactions may be conducted in solution, the waste associated with normal solid phase synthesis, in which large excesses of reagents are used to ensure complete reaction, is avoided.

The nanoscale synthesis system may also include a support structure for detachably retaining the various components of the system. The support structure can be of the "assembly board type" that will contain prearranged flow channels and connector ports. The desired components of the system can be fastened into these connectors by pins. The desired components will have the necessary fittings that allow them to be sealed with the pre-arranged or selectively located flow channels or connectors. The flow system can also include detachable mixing devices, e.g., static or ultrasonic, some of which can be "chip like" in design. The reaction units, whether "chip like" or not, can be of the thermal, electrochemical, photochemical, pressure type and be any shape, e.g., rectangular or cylindrical.

The separatory components can provide for membrane separation, concurrent or countercurrent flow extraction, chromatographic separation, electrophoretic separation, or distillation. The detectors can include electrochemical, spectroscopic or fluorescence based detectors to monitor the reactants, intermediates, or final products.

In accordance with the preferred embodiment of the present invention, an apparatus for achieving the systems described above is illustrated in FIGS. 1–10.

The basic concept of the subject invention is to produce a modular system, with components (reactors, separation chambers, analyzers, etc.) that are inexpensive and easily assembled. The subject invention can be assembled on a flow channel assembly board in the same way integrated circuitry chips and other electrical components are assembled on a circuit board. In the ICS system various reactors, analyzer(s), e.g., "chip units," are put together on an "assembly board". Two approaches to assembling such systems would be (a) custom design chips and assembly boards or, (b) the current capillary high pressure liquid chromatography (HPLC)-capillary zone electrophoresis (CZE) approach with microbore tubing (silica, stainless steel) and various connectors, injectors, pumps, etc. In case (a) the chips could be made from silica ($SiO_2$) (glass), silicon (Si) (as integrated circuit chips), polymers (plastic), and/or metal (stainless steel, titanium).

An example of fabricating a chip unit 100 according to the invention is shown in FIGS 1a–1d. With reference to FIGS. 1a–1d, a substrate of $SiO_2$ or Si is designed to include a rectangular reaction chamber 4, although other configurations, discussed below, are contemplated. The chamber 4 is formed by photolithographic processes such as those currently used for integrated circuits and circuit boards. A photoresist layer 2 is deposited on the upper surface 16 of the $SiO_2$ or Si block substrate 1 and, the desired pattern 3 is formed in layer 2 by exposure to the proper image and development techniques. The rectangular reactor chamber 4 is formed by etching the preformed pattern into the substrate, e.g., with HF for $SiO_2$ to the extent necessary to form a chamber having the desired volume. For complex structures, multiple photolithographic processes may be necessary. Flow channels for the reactor are similarly fabricated using photolithography from the other side of the substrate. A second photo-resist layer 7 is placed on lower surface 6, exposed to form port openings 8 and 9. Thereafter, channels 10 and 11 are formed to provide flow communication to reactor chamber 4. Finally, a cover is attached to close the upper surface 5 to form a top of the reactor 4 and produce the finished chip. Photoresist layers 2 and 7 also include a plurality of patterns 13–16 and 17–20 formed thereon so that through channels for fastening pins can be formed. The reactor could also be fabricated at one time, alternatively, with plastic materials, by injection molding or casting techniques. Micromachining (e.g., using the scanning tunneling microscope or scanning electrochemical microscope) of metals and semiconductor substrates could also be used to make the modular units of the subject invention.

Figure 10C:
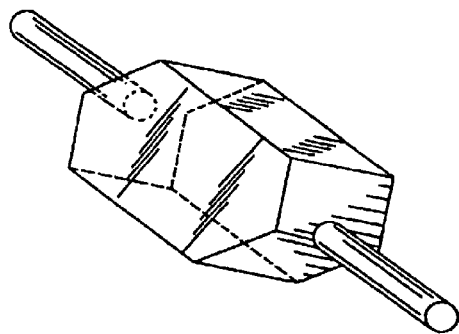
FIGS. 10a–10d show the shape of a variety of nanoscale reactors that can be used in the present invention.
Figure 10B:
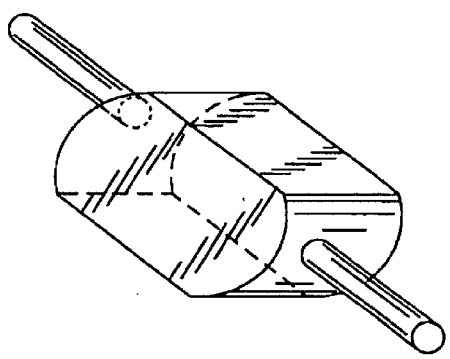
Figure 10D:
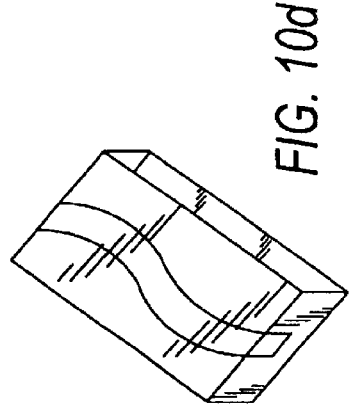
Figure 10A:
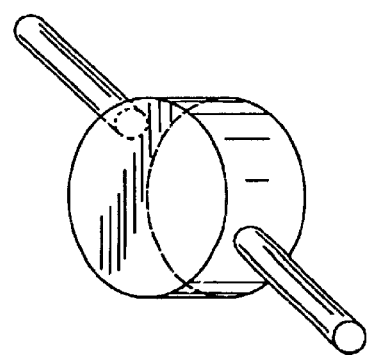

The shape of the reactor may be other than rectangular or cylindrical For example, FIG. 10a shows a circular chamber having planar upper and lower walls. FIG. 10b shows an essentially rectangular chamber where upstream and downstream ends are hemispherical in shape or as seen in FIG. 10c triangular. Triangular or curved inlet and/or outlet walls reduce any possible dead volume in the reactor. The reactor can also be serpentine in design to increase residence time, FIG. 10d.

The following chart depicts volume parameters for differing reactors of the present invention. More particularly, the chart depicts volume characteristics associated with two reactor configurations: (a) a cylindrical-shaped reactor; and (b) an elongated square-shaped reactor.

For a cylindrical reactor, the volume (V) is related to the diameter (d) and the length (L) by the following formula:

$$V=(\pi r^2)(L)=(\pi(d/2)^2)(L)=\pi d^2 L/4.$$

The first three columns (from left to right) depict the diameter, length, and corresponding volume for a cylindrical reactor.

For an elongated square reactor, the volume is related to the diameter (d) and the length (L) by the following formula:

$$V=d^2 L.$$

The last three columns (from left to right) depict the diameter, length, and corresponding volume for a elongated square reactor.

Note the following units in interpreting the following table:

| Symbol | Meaning | X = distance of 1 m | Y = volume of 1 $m^3$ (in liters) | |
|---|---|---|---|---|
| m | meter | 1 m | 1 $m^3$ | $1 \times 10^6$ mL |
| cm | decimeter | $1 \times 10^1$ dm | $1 \times 10^3$ $(dm)^3$ | $1 \times 10^6$ mL |
| cm | centimeter | $1 \times 10^2$ cm | $1 \times 10^6$ $(cm)^3$ | $1 \times 10^6$ mL |
| mm | millimeter | $1 \times 10^3$ mm | $1 \times 10^9$ $(mm)^3$ | $1 \times 10^6$ mL |
| μm | micrometer | $1 \times 10^6$ μm | $1 \times 10^{18}$ $(\mu m)^3$ | $1 \times 10^6$ mL |
| nm | nanometer | $1 \times 10^9$ nm | $1 \times 10^{27}$ $(nm)^3$ | $1 \times 10^6$ mL |
| pm | picometer | $1 \times 10^{12}$ pm | $1 \times 10^{36}$ $(pm)^3$ | $1 \times 10^6$ mL |
| fm | femtometer | $1 \times 10^{15}$ fm | $1 \times 10^{45}$ $(fm)^3$ | $1 \times 10^6$ mL |
| am | attometer | $1 \times 10^{18}$ am | $1 \times 10^{54}$ $(am)^3$ | $1 \times 10^6$ mL |

The relationship between cubic centimeters and liters follows: $cm^3 \cong 1$ mL.

| Cylindrical Reactor | | | Elongated Square Reactor | | |
|---|---|---|---|---|---|
| d ($\mu$m) | L ($\mu$m) | V ($\mu$L) | d ($\mu$m) | L ($\mu$m) | V ($\mu$L) |
| 1 | 10 | $7.85 \times 10^{-9}$ | 1 | 10 | $1.00 \times 10^{-8}$ |
| 1 | 100 | $7.85 \times 10^{-8}$ | 1 | 100 | $1.00 \times 10^{-7}$ |
| 1 | 1000 | $7.85 \times 10^{-7}$ | 1 | 1000 | $1.00 \times 10^{-6}$ |
| 1 | 10000 | $7.85 \times 10^{-6}$ | 1 | 10000 | $1.00 \times 10^{-5}$ |
| 10 | 10 | $7.85 \times 10^{-7}$ | 10 | 10 | $1.00 \times 10^{-6}$ |
| 10 | 100 | $7.85 \times 10^{-6}$ | 10 | 100 | $1.00 \times 10^{-5}$ |
| 10 | 1000 | $7.85 \times 10^{-5}$ | 10 | 1000 | $1.00 \times 10^{-4}$ |
| 10 | 10000 | $7.85 \times 10^{-4}$ | 10 | 10000 | $1.00 \times 10^{-3}$ |
| 100 | 10 | $7.85 \times 10^{-5}$ | 100 | 10 | $1.00 \times 10^{-4}$ |
| 100 | 100 | $7.85 \times 10^{-4}$ | 100 | 100 | $1.00 \times 10^{-3}$ |
| 100 | 1000 | $7.85 \times 10^{-3}$ | 100 | 1000 | $1.00 \times 10^{-2}$ |
| 100 | 10000 | $7.85 \times 10^{-2}$ | 100 | 10000 | $1.00 \times 10^{-1}$ |
| 1000 | 10 | $7.85 \times 10^{-3}$ | 1000 | 10 | $1.00 \times 10^{-2}$ |
| 1000 | 100 | $7.85 \times 10^{-2}$ | 1000 | 100 | $1.00 \times 10^{-1}$ |
| 1000 | 1000 | $7.85 \times 10^{-1}$ | 1000 | 1000 | 1.00 |
| 1000 | 10000 | 7.85 | 1000 | 10000 | 10.00 |

Figure 2:
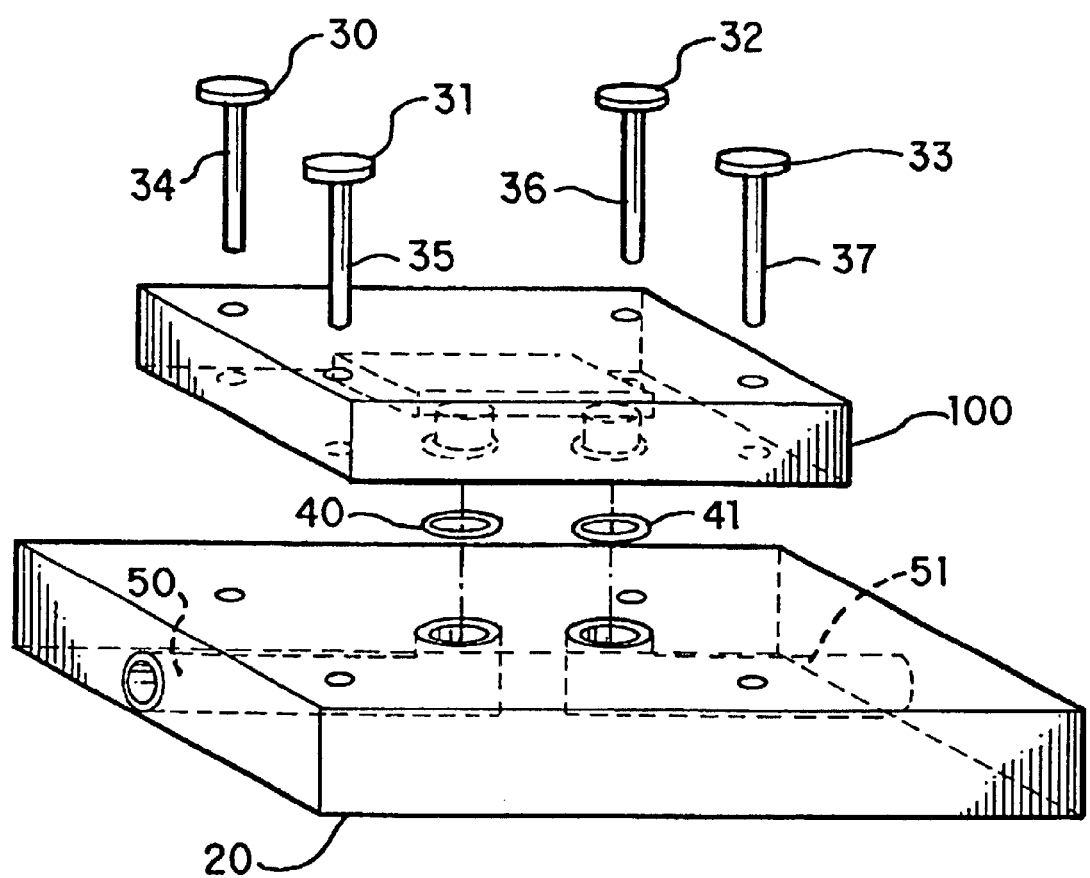
FIG. 2 illustrates an exploded view of a chip type reactor unit and the fluid delivery flow channels of an assembly board according to the present invention.

The different kinds of chip units produced according to the subject invention could then be connected to the assembly board containing the desired flow connections (FIG. 2) and also (not shown) electrical connections to electrodes, heaters, etc. FIG. 2 uses o-rings 40 and 41 TEFLON® (tetrafluorethylene (TFE) fluorocrbon polymers), VITRON® (fluorocarbon elastomers based on the copolymer of vinylidene fluoride and hexafluoropropylene) to connect the chip channels 10 and 11 to the corresponding channels 50 and 51 on asssembly board 20 and pins 30–37 (or clips) to hold the chip to board 20.

Figure 3:
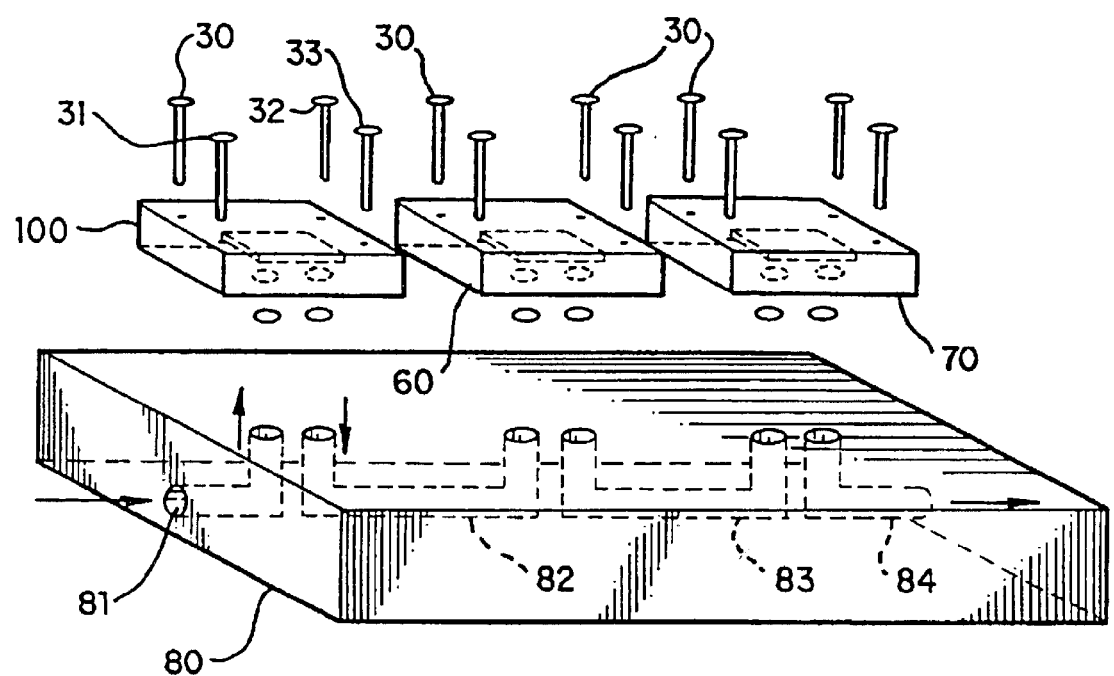
FIG. 3 is an exploded view of one embodiment of the ICS system

FIG. 3 shows an assembly of several different chips on a single board with interconnections. In FIG. 3 units 100, 60, and 70 are respectively a reactor, a separator and an analyzer. The housings for separator 60 and analyzer 70 are formed in a manner similar to that of reactor unit 100 described above, but include the requisite, structures and components to perform the designated process, e.g., separation, analysis. Pins 30–33 connect the units 100, 60 and 70 to assembly board 80 containing channels 81–84 therein. Channels 81 and 82 respectively communicate with channels 10 and 11 in reactor unit 100. Similarly, channels 82 and 83 communicate with the corresponding channels in unit 60 and channels 83 and 84 communicate with the channels in unit 70.

Alternatively capillary tubing for reactors, detectors, etc., following current HPLC-CZE practice, sized in accordance with the subject disclosure may be assembled on a support board in a similar manner (not shown).

For capillary tubing, connectors, pumps, etc., using the capillary HPLC approach, can be obtained from manufacturers, such as, Valco, Swagelok, and Waters speialized materials usefull in the subject invention reactors and separators can be made from NAFION® (a perfluoroionomer resin)(ion-exchange) hollow fibers and are manufactured by DuPont.

If a glass substrate is used for the "chip" units, the walls are already $SiO_2$. If a Si substrate is used, $SiO_2$ can be formed by oxidation in air under controlled temperature conditions. For metal substrates, e.g, Ti, a protective and insulating film ($TiO_2$) can also be formed by air or anodic oxidation. It is also possible to coat the walls of the tube with catalyst film, organic films for separations, etc.

Figure 4:
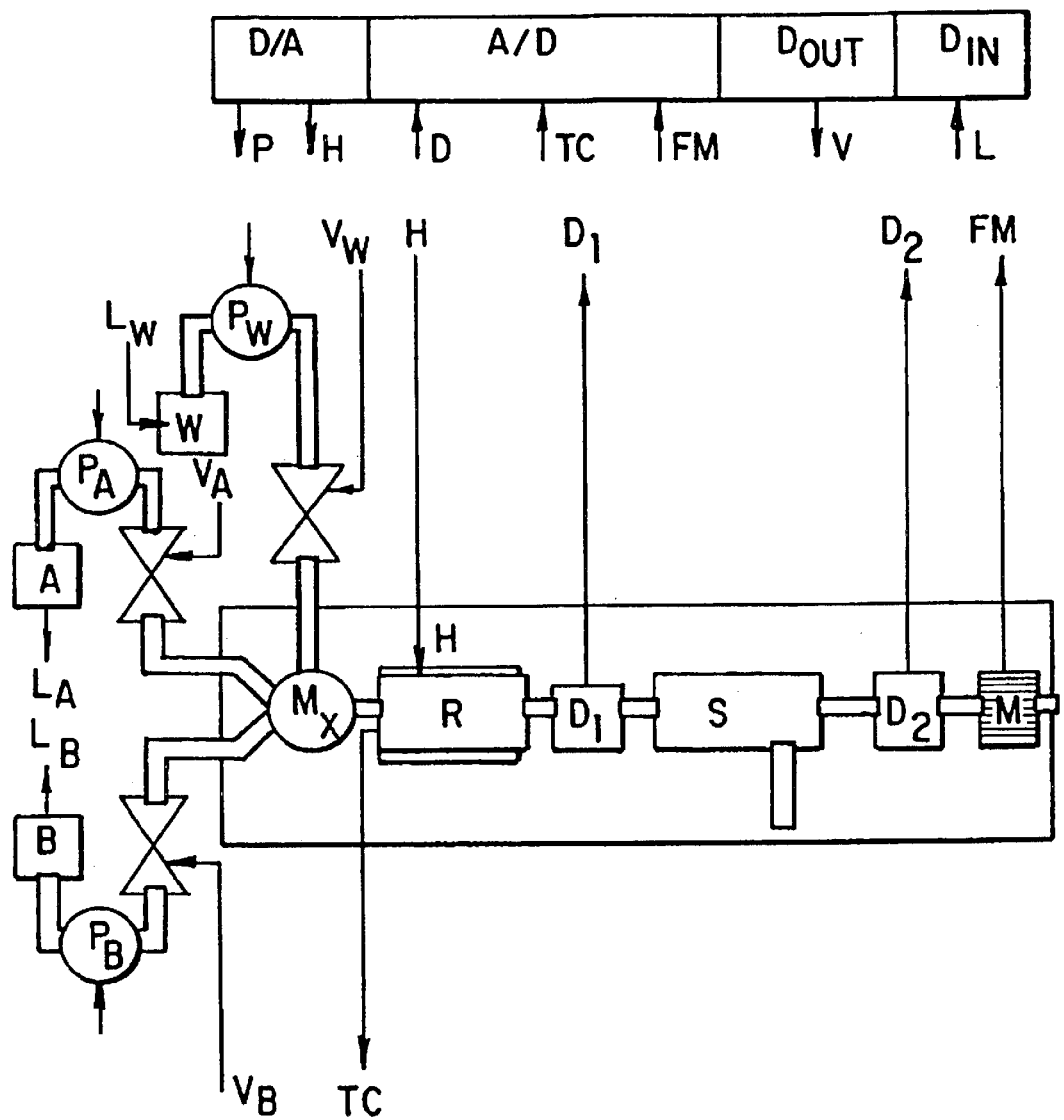
FIG. 4 shows an exemplary ICS system with fluid control and computer interfacing according to the subject invention.

FIG. 4 includes an assembly board schematically showing the "chip" type processing units of the subject invention. The assembly board includes a reactor R formed in a manner similar to unit 100 above, but includes a heat transfer system. The reactor R communicates with a chip type mixer Mx at the upstream end and a chip type detector D1, e.g., unit 100, at the downstream end. The detector D1 communicates with a chip type separator, e.g., unit 60, which in turn is in fluid communication with a second chip type detector unit D2, e.g., unit 70.

The system of FIG. 4 operates as follows: reagents A and B via pressure actuated pumps PA and PB, and valves VA and VB sequentially or simultaneously flow to the mixer MX. If isolation of a reagent is necessary, after reagent A is fed to mixer MX and discharged to the reactor R1, a wash fluid W is conveyed via pump PW and valve VW to the mixer MX and discharged. Signals from detectors D1, D2, thermocouple TC, and flowmeter FM are transmitted to the computer through interface 90 to control the flow of reagents A and B and temperature, or any additional reagents according to the process to be performed by the subject invention.

Having now generally described this invention, the following examples are included for purposes of illustration and are not intended as any form of limitation.

EXAMPLES 1–2

Diels-Alder Reactions

Organic synthesis via the Diels-Alder reaction involves a process in which two new carbon-carbon bonds and a new ring are formed by the reaction of a diene with a dienophile, where the $C_1$ and $C_4$ of the conjugated diene attach to the doubly-bonded carbon atoms of the unsaturated carbonyl compound (dienophile). Two variations are described below. In reaction [1], the reactants and the product are liquids while in reaction [2], one reactant and the product are solids.

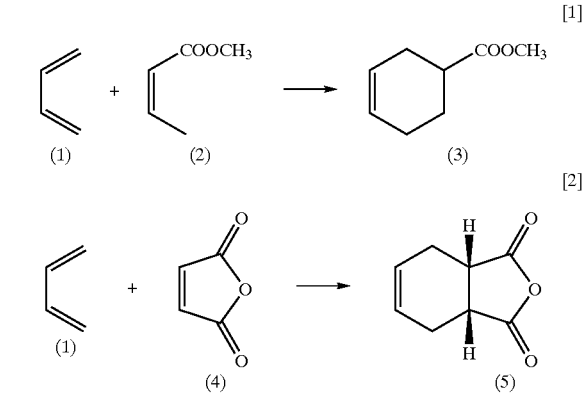

In each case the reaction occurs readily at room temperature, but they may be gently warmed to reduce the time required. These reactions are known to be very efficient when conducted on a typical laboratory scale.

In reactions [1] and [2] above, compound (1) can be a $C_4$–$C_6$ diene such as 1,3 butadiene, 1,4 pentadiene, 1,3 hexadiene, 2,4 hexadiene, 1,5 hexadiene, 1,3 pentadiene, 2 methyl, 1,3-butadiene and 2,3-dimethyl-1,3-butadiene. Generally most dienophile compounds are of the form C=C—$Z^1$ or $Z^1$—C=C—$Z^2$ where $Z^1$ and $Z^2$ are CHO, COR, COOH, COOR, COCl, COAr, $CH_2OH$, $CH_2Cl_2$, $CH_2NH_2$, $CH_2CP$, $CH_2COOH$, or halogen and R is a $C_1$–$C_6$ straight or branched carbon chain. Examples of dienophiles include but are not limited to acrolein, methyvinylketone, crotonaldehyde, dibenzlacetone, acrylonitrile, p-benzoquinone, napthaquinones.

EXAMPLES 3—4

1,4 Benzodiazelines Reactions 1,4-Benzodiazepines constitute one of the most important classes of bioavailable therapeutic agents with widespread biological activities. An exemplary starting material for these agents include the following compound where R' and R" can be hydrogen or lower alkyl ($C_1$—$C_5$) and R''' can be hydrogen, halogen, trifluoromethyl, amino, nitro, etc.:

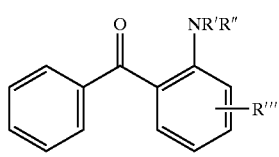

As seen below, diazepam (8), which is a well known tranquilizer, can be prepared according to equations 3 and 4 below, where an amide bond formation between 5 and 6 is induced following a standard amino acid coupling technique, and the intermediate amide 7 is cyclized by thermal, acid-catalyzed cyclocondensation to give 8 (eq 3).

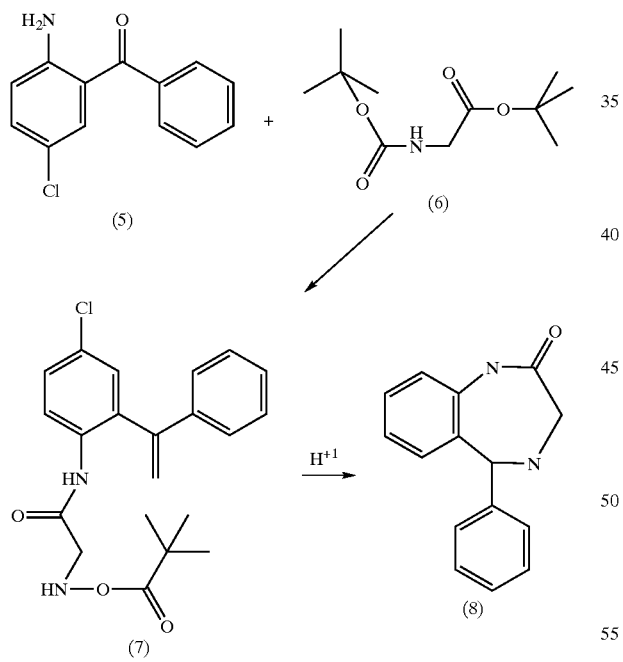

While it may be possible to conduct this series of steps in a single reactor, it can also be conducted in two reactors, the first reactor is designed for purely thermal reactions and, the second is designed to contain a suitable acid catalyst on a solid support. Another approach to forming (8) entails an initial condensation of a glycine ester (9) with the benophenone (5) to give the imine (10), which is then cyclized to give (8) (eq. 4).

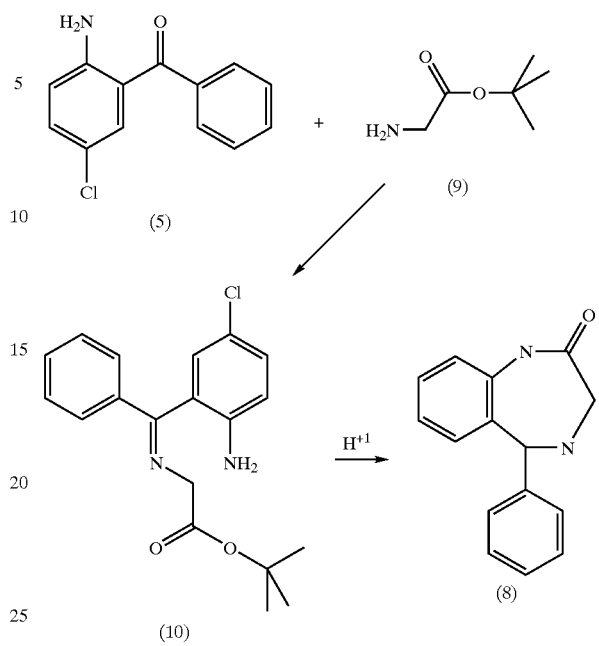

The more efficient of these two procedures will then be used to prepare a combinatorial library of benzodiazepine derivatives of the general structure 11 (depicted below) where X is hydrogen, lower alkyl ($C_1$ $C_5$), lower alkenyl or lower alkanoyl, and R', R", R''' are as defined above.

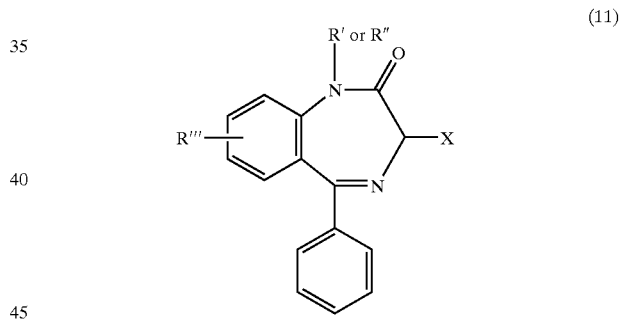

A diverse array of benzophenone and amino acid derivatives are commercially available, and these will be used according to the optimal sequence defined by the previous experiments. It is important to recognize that the combinatorial synthesis of benzodiazepine analogues by the proposed technology occurs in solution and thus has a number of important advantages over conventional solid phase synthetic techniques. For example, stoichiometric quantities of reactants and reagents may be used in these nanoreactors, whereas large excesses of one reactant or reagent are typically required in solid phase synthesis to ensure complete reaction. Each reaction is conducted in a separate reactor, and thus the conditions may be optimized for each pair of reactants, thereby increasing the overall efficiency with which the library may be generated. It should be possible to use infrared or ultraviolet detectors to monitor the progress of different reactions.

In order to apply nanotechnology to the parallel synthesis of a library of compounds, it is simply necessary to route parallel streams of reactants into different reactors. After one reaction is completed, the products from each reaction may be transferred to another reactor for reaction with the next reactant. Lithographic techniques described above are used to design the "plumbing", and since the precise routing can be programmed, the identification of each compound that emerges from the various reactors is known. Thus, the laborious "tagging" of compounds in the library, which is common to many solid phase protocols, is unnecessary.

EXAMPLE 5

Electrochemically Catalyzed Hydrogenation Reaction

The reduction of an isolated carbonarbon bond by hydrogenation constitutes a useful transformation in organic synthesis. In order to develop an electrochemical redox reactor capable of effecting this conversion, the reduction of the Diels-Alder adduct 3 according to equation 6 is considered.

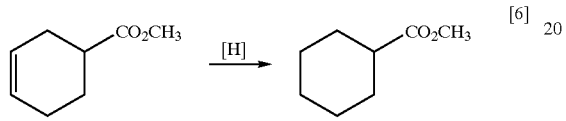

[6]

The reactor will consist of an electrochemical cell with a platinum black cathode useful for electrocatalytic hydrogenations in protic solvents. Such protic solvents include water and alcohols. This reactor is linked with the thermal reactor used to prepare 3 to conduct the entire sequence in a single manufacturing operation.

EXAMPLE 6

Thermal Conversion Reaction

Figure 5:
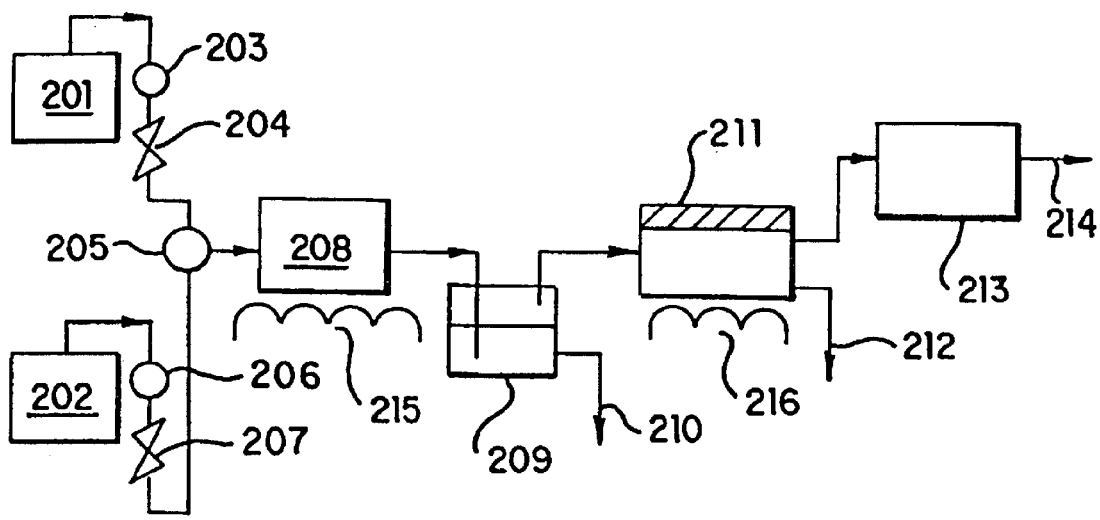
FIG. 5 is a flow chart for preparing t-BuCl using the subject invention.

With reference to FIG. 5, solutions of concentrated hydrochloric acid 201 and t-butanol 202 are metered through pumps 203, 206 and valves 204, 207 to a mixer 205 to the reaction chamber 208. Temperature in the reaction chamber 208 is controlled via a heating/cooling system 215 on the assembly board, e.g., 80, to maintain the reaction temperature (measured by a thermocouple) at about 30–30° C. The two phases that form are separated in the separator chamber 209 and further purification of t-BuCl can be accomplished, if desired, by distillation at 50° C. in chamber 213 with product being withdrawn via line 214. HCl and H$_2$O are withdrawn via line 210 and waste is discharged via line 212. This thermal conversion reaction can be depicted by the following:

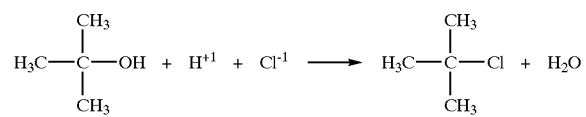

EXAMPLE 7

Photochemical Conversion Reaction

Figure 6:
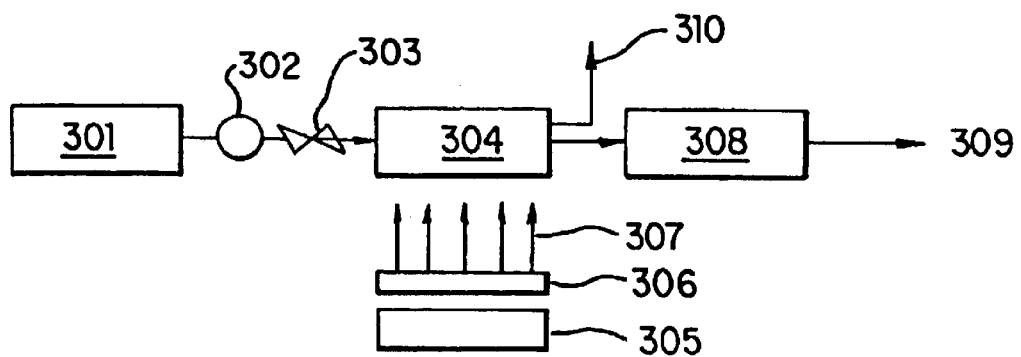
FIG. 6 shows a flow chart for photochemical conversion of dibenzylketone using the ICS system of the subject invention.

With reference to FIG. 6, dibenylketone (DBK) in benzene 301 (0.01 M) is metered via 302 and 303 into the photochemical reaction chamber 304 with at least one transparent wall, where it is irradiated with light 307 from a 450 watt xenon lamp 305 via filter 306. The CO produced 310, in the reaction 309 is vented and the dibenzyl product is purified, if desired, through a chromatographic separator 308 and withdrawn through line 309. This photochemical conversion reaction can be depicted by the following:

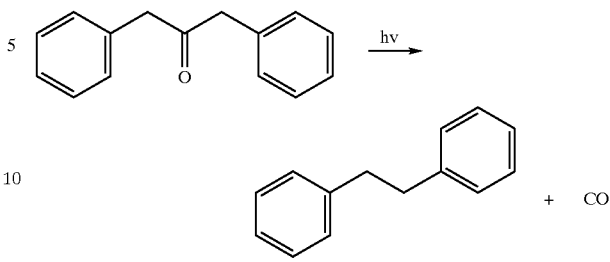

EXAMPLE 8

Electrochemical Reduction Reaction

Figure 7:
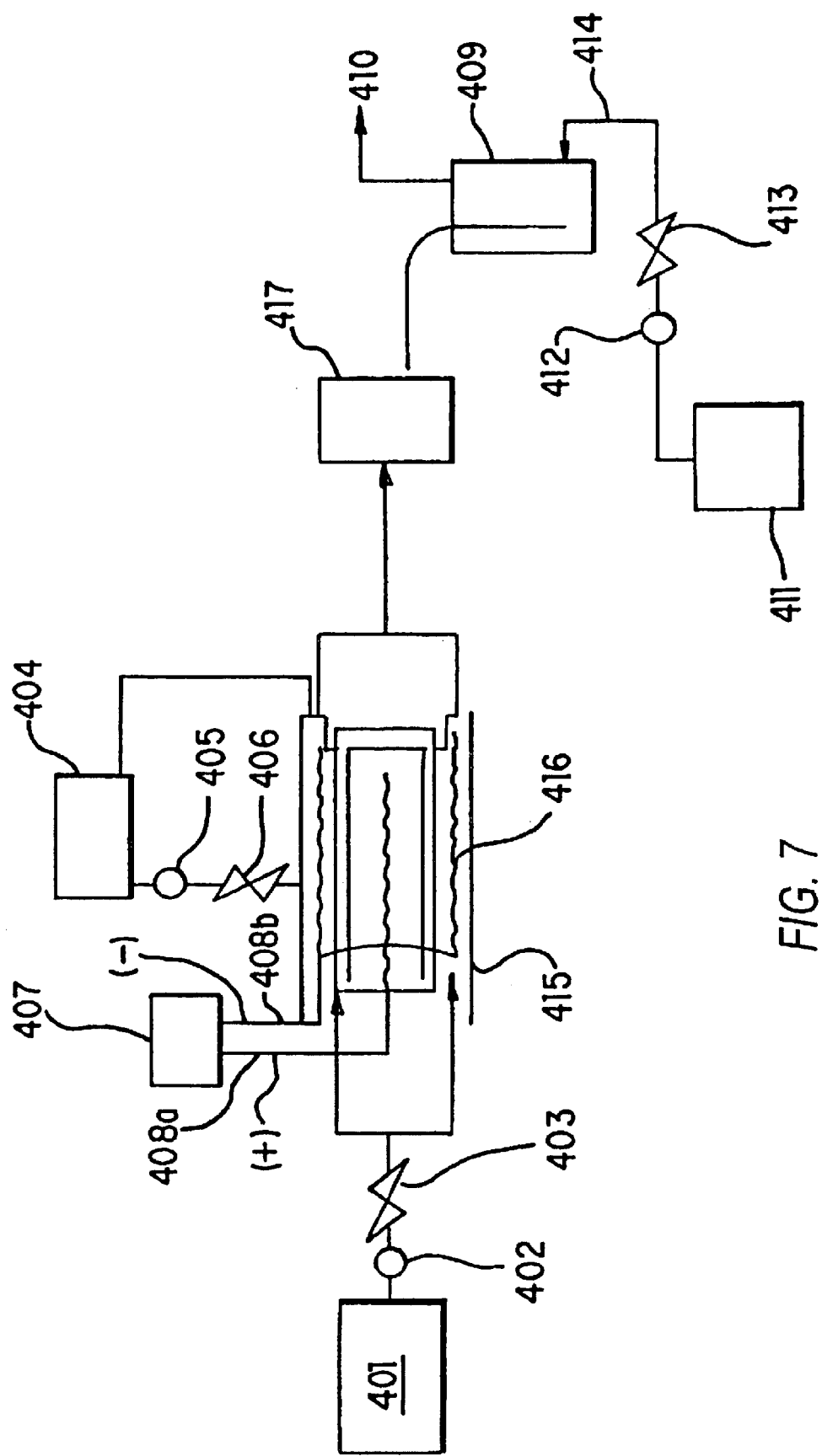
FIG. 7 is a flow chart illustrating electrochemical reduction of benzoquinone according to the present invention.

In FIG. 7, an acidic aqueous solution of benzoquinone (0.1 M) 401 is metered (402, 403) into the cathodic chamber 416 of the electrochemical reactor 415. This chamber, e.g. outside a Nafion hollow fiber tube containing the Pt anode and the analyte, contains a carbon or zinc cathode. Anode 408a and cathode 408b are connected to a power supply 407. The current density and flow rate are controlled to maximize current efficiency as determined by analysis of hydroquinone by the electrochemical detector 417. Hydroquinone 410 is extracted in extractor 409 from the resulting product stream with ether 414 metered (412 and 413) from ether supply 411. Alternatively, flow in chamber 415 can be directed to the inner anode chamber with the appropriate controls. This electrochemical reduction reaction can be depicted by the following:

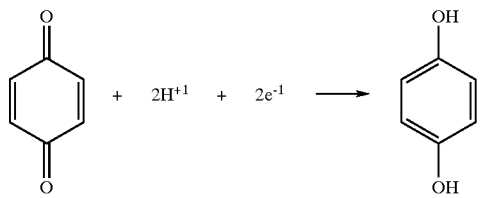

EXAMPLE 9

Enzyme-Catalyzed Conversion Reaction

Figure 8:
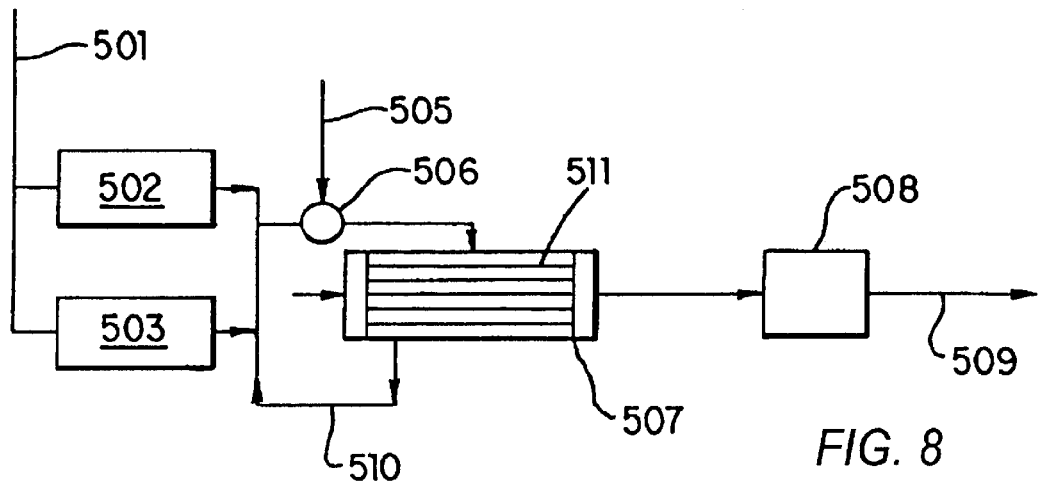
FIG. 8 is a flow chart for multiphase membrane reactor conversion of benzylpenicillin (BP) to 6 amino penicillanic acid (6-APA) using the ICS system.

In FIG. 8, the effluent 501 from a penicillin fermentation reactor containing benzylpencillin (BP) is fed through a filter bank 502 and 503. An aqueous acid 505 is mixed with the filtered BP in mixer 506 and fed to membrane reactor 507. The membrane reactor 507 is preferably a hollow fiber tube 511 on which the enzyme penicillin acylase has been immobilized. The tube also selectively extracts 6-aminopencillanic acid (6-APA) (see J. L. Lopez, S. L. Matson, T. J. Stanley, and J. A. Quinn, in "Extractive Bioconversions," Bioprocess Technologies Series, Vol. 2, B. Masttgiasson and O. Holst. Eds., Marcel Dekker, N.Y., 1987). The BP is converted on the wall of the fiber and the product passes into the sweep stream inside the fiber where it can be purified by ion exchange 508. The BP stream 510 is recycled back through the reactor. This enzyme catalyzed conversion reaction can be depicted by the following:

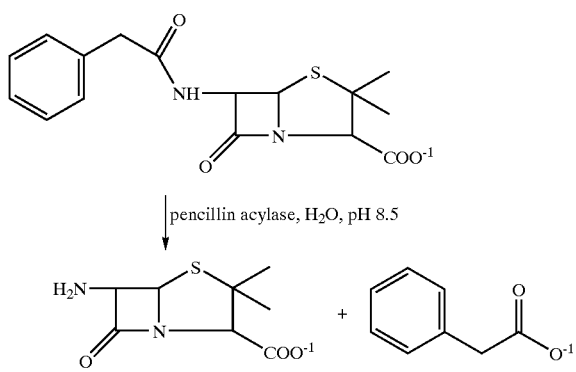

EXAMPLE 10

Catalytic Conversion Reaction

Figure 9:
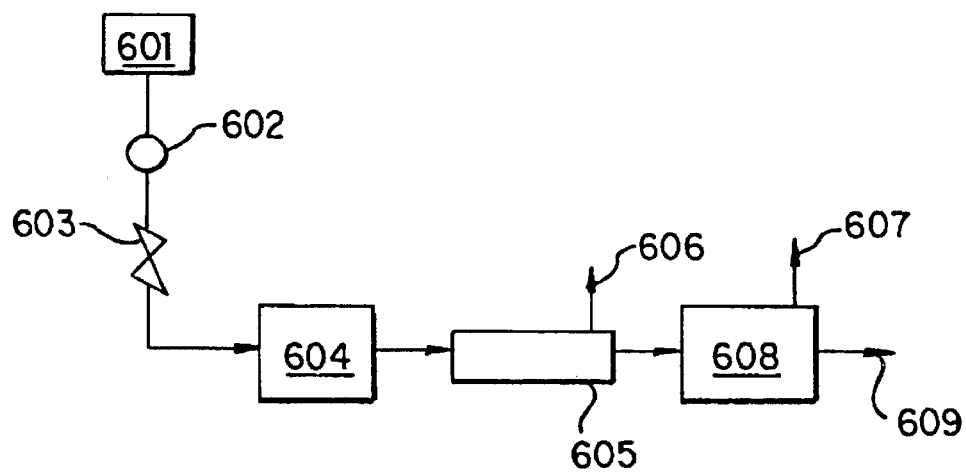
FIG. 9 is a flow chart for converting n-$C_7H_{16}$ to toluene using the subject invention.

In FIG. 9, liquid n-heptane 601 is metered via 602, 603 into the vaporizing chamber 604 held at 150° C. The vaporized heptane is then conveyed to the catalytic reactor 605 containing a packed bed of $Pt/Al_{2O3}$ catalyst held at 400° C. Hydrogen is removed through line 606. The heptane-toluene mixture from reactor 605 is fed to separator 608 with toluene being removed through line 609 and heptane through line 607. This catalytic conversion reaction can be depicted by the following:

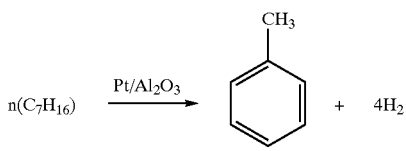

Although the invention has been described in conjunction with the specific embodiments, it is evident that many alternatives and variations will be apparent to those skilled in the art in light of the foregoing description. Accordingly, the invention is intended to embrace all of the alternatives and variations that fall within the spirit and scope of the appended claims, further, the subject matter of the above cited United States Patents are incorporated herein by reference.

I claim:

1. A modular chemical reaction system for performing a predetermined chemical process, the system comprising:
   (a) a plurality of modular, detachable reaction system components including at least a first reactor having a reaction volume of between 0.1 and 1000 nL, said reaction system components including reaction system component fluid connector ports; and
   (b) a support structure for detachably supporting said plurality of reaction system components, said support structure comprising support structure fluid connector ports that connect to said reaction system component fluid connector ports and flow channels that permit flow communication between said plurality of reaction system components;
   wherein said plurality of reaction system components are selectively arranged on and fastened to said support structure to accommodate said predetermined chemical process and wherein said plurality of reaction system components are capable of being selectively added, replaced and/or interchanged to accommodate a variety of different predetermined processes.

2. The system of claim 1, wherein said first reactor is selected from the group consisting of electrochemical, thermal, condensation, photochemical, reduction, and oxidation reactors.

3. The system of claim 1, wherein said plurality of reaction system components further comprise at least a second reactor having a reaction volume of between 0.1 and 1000 nL, said first reactor and said second reactor being connected in series.

4. The system of claim 3, wherein at least one of said first reactor or said second reactor has at least one wall formed from a material selected from the group comprising glass, metal, and synthetic polymer.

5. The system of claim 3, wherein at least one of said first reactor or said second reactor contains an acid/base catalytic coating.

6. The system of claim 3, wherein at least one of said first reactor or said second reactor contains a coating to facilitate a Diels-Alder reaction.

7. The system of claim 3, further comprising:
   (a) reactant containers for storing separate reactant supplies, wherein said reactant containers are adapted to supply said reactant supplies to at least one of said first reactor or said second reactor.

8. The system of claim 7, wherein said first reactor and said second reactor are arranged on said support structure and said flow channels are configured to permit cross-mixing of products from said first reactor and said second reactor.

9. A kit for a modular, selectively reconfigurable chemical reaction system having detachably assembled modular reaction system components wherein said modular reaction system components can be added, replaced and/or interchanged, comprising:
   (a) a plurality of modular, detachable reaction system components including at least a first reactor having a reaction volume of between 0.1 and 1000 nL, said reaction system components including reaction system component fluid connector ports; and
   (b) a support structure for detachably supporting said plurality of reaction system components, said support structure comprising support structure fluid connector ports that connect to said reaction system component fluid connector ports and flow channels that permit, upon connection of the connector ports, flow communication between said plurality of reaction system components;
   wherein said plurality of reaction system components are capable of being selectively arranged on and fastened to said support structure to accommodate a predetermined chemical process.

10. The kit of claim 9, further comprising at least a second reactor having a chamber volume of between 0.1 and 1000 nL.

11. The kit of claim 9, wherein said flow channels and said chamber volumes are formed from, or coated with, $SiO_2$.

12. The system of claim 7, wherein said reactant supplies are a diene and a dienophile.

13. The system according to claim 3, wherein said first reactor and said second reactor are arranged on said support structure and said flow channels are configured to permit cross-mixing of products.

14. The system according to claim 1 wherein at least two of the reaction system components operate in series.

15. The system according to claim 1 wherein at least two of the reaction system components operate in parallel.

16. The system according to claim 1 further comprising:
(a) reactant containers for storing separate reactant supplies, wherein said reactant containers are adapted to supply said reactant supplies to two or more of said reaction system components operating in parallel.

17. The system according to claim 1 further comprising:
(a) reactant containers for storing separate reactant supplies, wherein said reactant containers are adapted to supply said reactant supplies to two or more of said reaction system components operating in series.

18. The system according to claim 1 wherein one or more of said plurality of reaction system components are arranged on said support structure and said flow channels are configured to permit said one or more reaction system components to carry out one or more intermediate reactions.

19. The system according to claim 18 wherein the one or more intermediate reactions are carried out in series and/or in parallel.

20. The system according to claim 1 further comprising one or more additional assemblies of modular chemical reaction systems to scale-up the reaction.

21. The system according to claim 20 wherein the additional assemblies are added in parallel.

22. The system according to claim 1 wherein said plurality of reaction system components are arranged on said support structure and said flow channels are configured to permit said predetermined chemical reaction to be performed in parallel in the plurality of reaction system components.

23. The system according to claim 1 wherein said plurality of reaction system components are arranged on said support structure and said fluid channels are configured so that said plurality of reaction system components includes two or more reaction system components that operate in series and two or more different reaction system components that operate in parallel.

* * * * *